US008033829B2

(12) United States Patent
Besson

(10) Patent No.: US 8,033,829 B2
(45) Date of Patent: Oct. 11, 2011

(54) TOOTH PREPARATION SOLUTION AND METHOD

(76) Inventor: Frank R. Besson, Scotch Plains, NJ (US)

(*) Notice: Subject to any disclaimer, the term of this patent is extended or adjusted under 35 U.S.C. 154(b) by 303 days.

(21) Appl. No.: 11/879,437

(22) Filed: Jul. 17, 2007

(65) Prior Publication Data

US 2009/0023114 A1 Jan. 22, 2009

(51) Int. Cl.
*A61C 5/00* (2006.01)
(52) U.S. Cl. ........................ 433/228.1
(58) Field of Classification Search .............. 433/2, 6, 433/88, 9, 228.1, 89, 90, 215; 451/90, 102; 264/16; 216/34, 96, 101, 103; 252/79.2
See application file for complete search history.

(56) References Cited

U.S. PATENT DOCUMENTS

| | | | | |
|---|---|---|---|---|
| 3,789,462 A * | 2/1974 | Reich | | 433/166 |
| 3,955,282 A * | 5/1976 | McNall | | 433/9 |
| 4,802,950 A | 2/1989 | Croll | | |
| 5,133,957 A | 7/1992 | Suh et al. | | |
| 5,425,641 A * | 6/1995 | Fischer | | 433/226 |
| 5,739,177 A * | 4/1998 | Ohno et al. | | 523/118 |
| 5,759,039 A * | 6/1998 | Kunstadter et al. | | 433/215 |
| 6,025,025 A | 2/2000 | Bartrug et al. | | |
| 6,660,250 B1 * | 12/2003 | Higgins | | 424/49 |
| 6,994,551 B2 * | 2/2006 | Wang et al. | | 433/226 |
| 7,160,108 B2 | 1/2007 | Jaffe | | |
| 2004/0039078 A1 * | 2/2004 | Suh et al. | | 523/113 |
| 2005/0176844 A1 * | 8/2005 | Aasen et al. | | 523/118 |
| 2006/0072958 A1 * | 4/2006 | Tsaur | | 401/132 |
| 2008/0286724 A1 * | 11/2008 | Wong et al. | | 433/228.1 |

OTHER PUBLICATIONS

ETCH-RITE IFU; Pulpdentò Corporation; ETCH-RITE Dental Etching Gel Instructions for Use; http://www.pulpdent.com/bonding/etchinst.html; Feb. 2, 2007; 5 pages.
ORTHO-TWOO Orthodontic Direct Bonding System (Paste/Paste) Self-Cured; http://www.bisco.com/instructions/orthotwo_instr_print.asp; Feb. 2, 2007; 2 pages.
Mendes et al., Wear Aftr Microabrasion of Human Enamel With Different Forumulations and Number of Applications; V. 7, n. 1/2, p. 35-40, Jan./Jun. 1999; 6 pages.
3M Material Safety Data Sheet 3M Unitek Etching Liquid (704-037) Nov. 12, 2004; 7 pages.
JADA Coninuing Education; An evaluation of a technique to remove stains from teeth using microabrasion; Price et al.; http://jada.ada.org/cgi/content/full/134/8/1066; Feb. 2, 2007; 22 pages.
FOB; Mendes RF; Wear after microabrasion of human enamel with different forumulations and number of applications. Rev Fac Odontol Bauru Jan./Jun. 1999; 7 (½): 35-40; http://fob.usp.br/revista/conteudos/resumos1999/1999_1_ing/Abstract6.htm; Feb. 2, 2007; 1 page.
International Search Report issued on Oct. 6, 2008 in connection with International Application No. PCT/US08/08680.
Sturdevant et al., "The Art and Science of Operative Dentistry", Third Edition, pp. 541-572 (1994). Baum et al., "Textbook of Operative Dentistry", Third Edition, pp. 243-247 (1995).
Graber et al., "Orthodontics Current Principles and Techniques", pp. 542-551 (1994).
Proffit et al., "Contemporary Orthodontics", The C.V. Mosby Co., pp. 294-295 (1986).

* cited by examiner

*Primary Examiner* — Cris L Rodriguez
*Assistant Examiner* — Sunil K Singh
(74) *Attorney, Agent, or Firm* — Lerner, David, Littenberg, Krumholz & Mentlik, LLP

(57) ABSTRACT

A method of preparing teeth for the adhesion of a component includes applying to at least one tooth a solution of liquid phosphoric acid and an abrasive such as pumice, removing the solution, and applying an adhesive for placing a component on the teeth.

15 Claims, 2 Drawing Sheets

TOOTH PREPARATION SOLUTION AND METHOD

BACKGROUND OF THE INVENTION

In the orthodontal and dental arts, it is known that prior to affixing orthodontal and dental components, such as braces and bondings, for example, it is necessary to prepare the teeth. This often involves cleaning the teeth thoroughly and preparing the teeth for adhesion of the components. Poor preparation can lead to premature failure of the adhesion.

The teeth may be cleaned using a prophy cup attached to a dental handpiece with prophy paste, then rinsed with water. Thereafter, a solution containing phosphoric acid is applied to each affected tooth for a period of time. Care must be taken in applying the phosphoric acid so as not to leave an excess in contact with the gums and with the surrounding tissue. The phosphoric acid is then washed away with water to avoid damage to gums and teeth. These steps provide for an opening of the enamel tubules that will facilitate bonding of an orthodontal or dental component.

The preparation of the teeth in such a manner can be mechanically demanding of the orthodontist or dentist, particularly in connection with a set of braces. The process requires several ingredients and numerous steps, and can become cumbersome and tedious.

U.S. Pat. No. 4,802,950 to Croll seeks to provide an alternate method for preparing teeth for bonding. Brace adhesion is not addressed at all in Croll. Croll teaches a gel etchant containing phosphoric acid, fumed silica, and silicon carbide particles. Croll states that phosphoric acid etchant, in liquid or gel composition is known. However, Croll dislikes the liquid form of phosphoric acid because, Croll argues, it is characterized by "uncontrolled flow" over the surfaces of the teeth. Croll prefers the gel because, he states, it holds its position on the teeth better. Despite Croll's teaching away from liquid etchants over twenty years ago, it is believed that currently, dentists and orthodontists prefer using the pumice and then a liquid phosphoric acid. The pumice and the liquid phosphoric acid are more effective and less expensive that Croll's method. Further, careful placement of the gel on the teeth is required so as to avoid the gel from contacting the gums and other tissue. In addition, because of the nature of gels, the rinsing process is more difficult.

Thus, an inexpensive, yet still effective, method and product are desired to prepare the teeth. Preferably a novel method and product would be easy to use, reduce the number of steps involved in preparing the teeth and/or increase the effectiveness of the bonding surface through superior preparation.

SUMMARY OF THE INVENTION

In one embodiment of the present invention, a method of preparing teeth for the adhesion of a component includes, applying to at least one tooth a solution of liquid phosphoric acid and an abrasive such as pumice, removing the solution, and applying an adhesive for placing a component on the at least one tooth.

In another embodiment of the present invention, a method of preparing teeth for the adhesion of a component includes, cleaning the tooth/teeth with a prophy paste, removing the prophy paste, applying a solution of liquid phosphoric acid and an abrasive such as pumice, removing the solution, and applying an adhesive for placing a component on the at least one tooth.

DETAILED DESCRIPTION

In an embodiment of the present invention, a solution is provided that combines an abrasive agent such as pumice and liquid phosphoric acid. Combining a liquid phosphoric acid solution and the pumice can reduce the number of steps required to prepare teeth for adhesion of various orthodontal and dental components while providing superior results. Even where the same number of steps are used, the results are better than a method without the solution.

The liquid phosphoric acid and abrasive solution is produced by adding a liquid phosphoric acid solution to powdered pumice. The pumice may be fine, medium or coarse, or among those pumices which break down to become more fine as they are used. Any suitable abrasive may be used.

The liquid phosphoric acid solution is generally of between, about, 30% and 40% by weight phosphoric acid. Preferably, the phosphoric acid is between, about, 35-37% phosphoric acid by weight. However, other suitable concentrations can be used, and in fact, other suitable acids or other suitable liquids can be used in place of the phosphoric acid.

A liquid is defined by Dictionary.com as, "composed of molecules that move freely among themselves but do not tend to separate like those of gases; neither gaseous nor solid; of, pertaining to, or consisting of liquids; flowing like water." In contrast, a gel is defined as, "a semirigid colloidal dispersion of a solid with a liquid or gas, as jelly, glue, etc.," also by Dictionary.com.

Croll preferred a gel substance and taught away from liquids, because Croll believed the liquids were uncontrollable. But Croll and others failed to find, as has now been found, that the addition of pumice to the liquid phosphoric acid greatly aids in controlling the flow of the liquid solution. The pumice in the liquid helps assist in keeping the liquid solution on the teeth. Phosphoric acid is corrosive and colorless; therefore, it can be challenging to use phosphoric acid separately. The addition of pumice allows the liquid solution to be easily identified and the practitioner can readily control the application and removal of the liquid solution.

Typically, a ratio of 1/3 pumice and 2/3 etchant is used. However, many other ratios are acceptable. For example, 2 parts pumice to 3 parts etchant may also be used.

Figure 1:
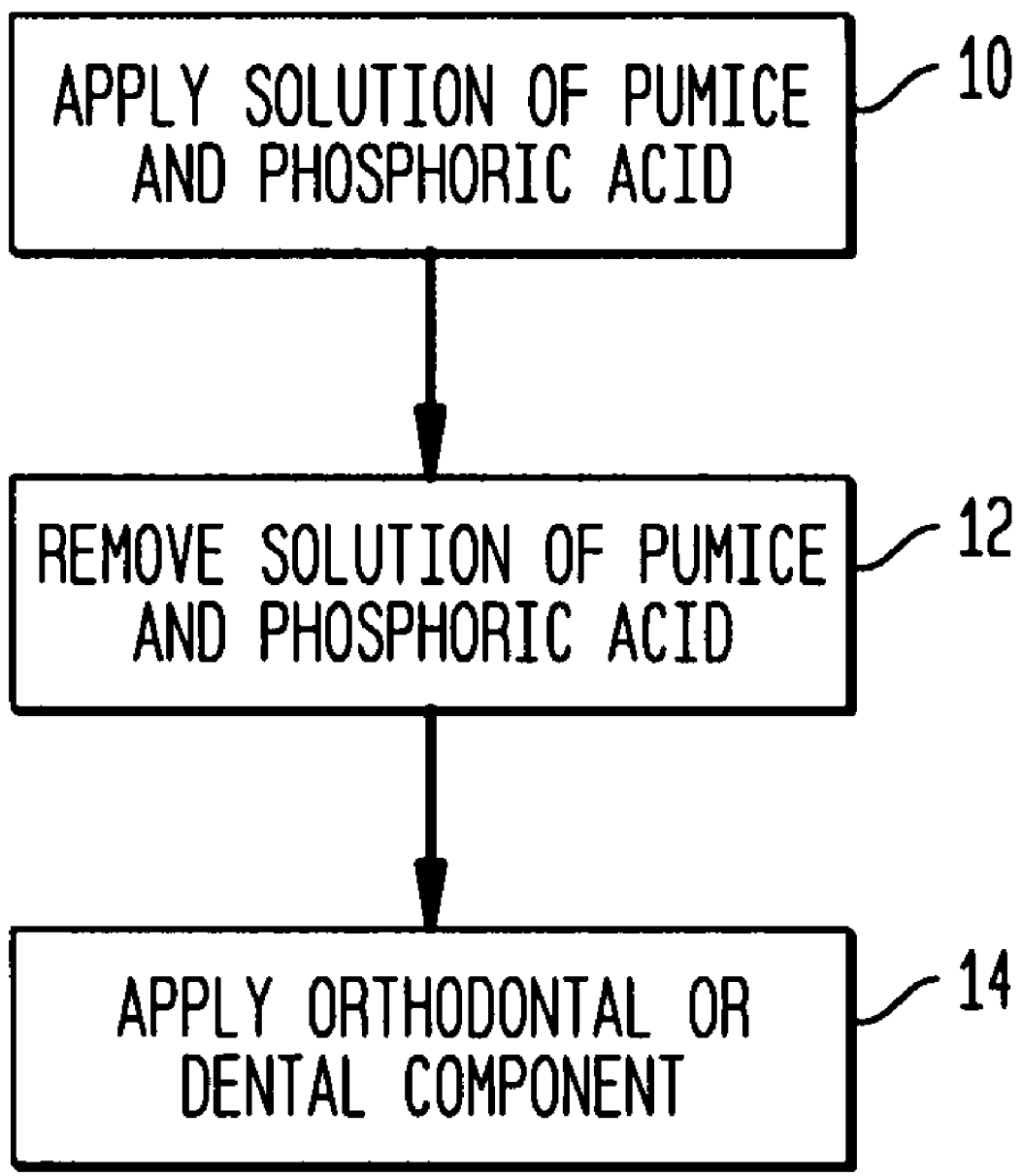
FIG. 1 is a depiction of a first embodiment of the present invention.

In one embodiment of the present invention, preparing the teeth for adhesion to orthodontal or dental components using the liquid solution of the present invention includes the steps as depicted in FIG. 1.

At step 10, the solution of pumice and phosphoric acid is applied. The solution may be applied using any suitable instrument, such as a swab or the like. The solution is then rubbed on the teeth for a short time. For example, the solution may be rubbed on the teeth for between, about, 10-30 seconds. Preferably, it is rubbed on for about 20 seconds. Then, the solution is left on the teeth for between, about, 30 and 60 seconds. Preferably, the solution is left on the teeth for about 40 seconds. Care must be taken to avoid long periods of contact so as not to damage the teeth.

The solution is then removed from the teeth, at step 12. Any suitable method may be used, including, for example, rinsing the teeth with water. The surfaces are then dried. Thereafter, orthodontal or dental component may be affixed in any appropriate manner, as at step 14.

Figure 2:
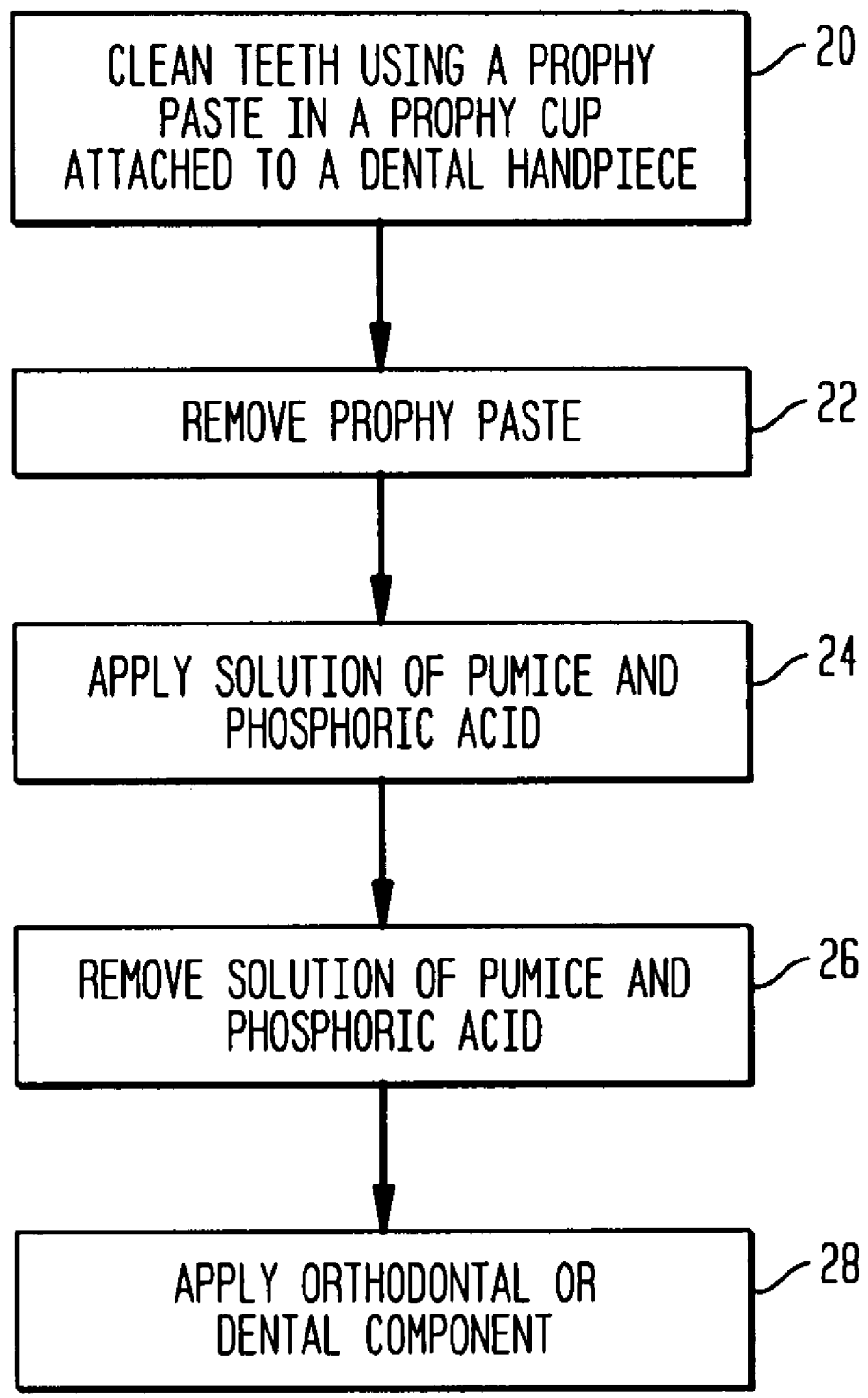
FIG. 2 is a depiction of a second embodiment of the present invention.

In a second embodiment of the present invention, depicted in FIG. 2. At step 20 the teeth are cleaned with prophy paste using a prophy cup attached to a dental handpiece. The prophy paste is then removed by any suitable method, as at step 22. For example, the teeth may be rinsed with water. At step 24, the liquid solution of phosphoric acid and pumice is applied, using a swab for example. The liquid solution is rubbed on and left on the teeth for a period of time as stated previously. Then, at step 26, the liquid solution is removed in any suitable manner. For example, the teeth may be rinsed with water. Finally, at step 28, a dental or orthodontal component is applied to the teeth.

Thus, in an embodiment of the present invention, this solution of the pumice and the phosphoric acid overcomes the difficulties Croll finds with the liquid without resort to a gel. The addition of the pumice aids in controlling the flow of the liquid while still retaining the rinsability of the liquid. Further, adding an abrasive to the phosphoric acid improves the cleaning effect of the etchant solution. Liquid phosphoric acid solutions are also very reasonably priced, and when used, as in an embodiment of the present invention, provide a solution which is readily seen, is easy to use and provides an effective way to prepare the teeth for adhesion to orthodontal and dental components, particularly for the adhesion of brace brackets.

Although reference has been made to preparing teeth, it should be noted that a single tooth or a few teeth may also be prepared in the manner as described herein.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of preparing teeth for the adhesion of a component, comprising:
    applying to at least one tooth in a single step a solution of liquid phosphoric acid and pumice, wherein the liquid phosphoric acid is in non-gel form, and wherein the solution is prepared prior to the step of applying the solution;
    removing the solution; and
    applying an adhesive for placing a component on the at least one tooth.

2. The method of claim 1, wherein the phosphoric acid comprises between about 30 and 40% phosphoric acid by weight.

3. The method of claim 2, wherein the phosphoric acid comprises between about 35 and 37% phosphoric acid by weight.

4. The method of claim 1, wherein the pumice comprises coarse, medium or fine particles.

5. The method of claim 1, wherein the pumice comprises particles which break down during use to become more fine during use.

6. The method of claim 1, wherein applying the solution is performed by dabbing the teeth with a swab dipped in the solution.

7. The method of claim 1, further comprising the step of cleaning the teeth by applying a prophy paste using a dental handpiece and a prophy cup.

8. The method of claim 1, wherein the solution of pumice and liquid phosphoric acid is massaged on the teeth for a period of between, about 10 and 30 seconds.

9. The method of claim 1, further comprising the step of allowing the solution of pumice and liquid phosphoric acid to remain in contact with the teeth for a period of between, about 30 and 60 seconds.

10. The method of claim 1, wherein the component is a bracket for braces being applied to the teeth, and includes the application of adhesive and placement of brackets on several teeth, and interconnecting the brackets to brace the teeth as appropriate to treat a particular condition of the teeth.

11. The method of claim 1, wherein the solution comprises 1/3 pumice and 2/3 phosphoric acid.

12. A method of preparing teeth for the adhesion of a component, comprising:
    applying a prophy paste to at least one tooth;
    removing the prophy paste;
    applying to at least one tooth in a single step a solution of liquid phosphoric acid and pumice, wherein the liquid phosphoric acid is in non-gel form, and wherein the solution is prepared prior to the step of applying the solution;
    removing the solution; and
    applying an adhesive for placing a component on the at least one tooth.

13. The method of claim 12, wherein the phosphoric acid comprises between about 30 and 40% phosphoric acid by weight.

14. The method of claim 12, wherein the phosphoric acid comprises between, about 35 and 37% phosphoric acid by weight.

15. The method of claim 12, wherein the solution comprises 1/3 pumice and 2/3 phosphoric acid.

* * * * *